(12) United States Patent
Feaster et al.

(10) Patent No.: US 7,775,991 B2
(45) Date of Patent: Aug. 17, 2010

(54) DEVICE FOR SAMPLING BLOOD

(75) Inventors: Shawn R. Feaster, Duluth, GA (US);
Rosann M. Kaylor, Cumming, GA (US); David S. Cohen, San Bruno, CA (US); Udo Leuschner, Regensburg (DE); Michael Strehl, Pfreimd (DE)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 222 days.

(21) Appl. No.: 11/217,091

(22) Filed: Aug. 31, 2005

(65) Prior Publication Data
US 2007/0049959 A1  Mar. 1, 2007

(51) Int. Cl.
*A61B 5/00* (2006.01)
*A61B 17/14* (2006.01)
*A61B 17/32* (2006.01)
*B65D 81/00* (2006.01)

(52) U.S. Cl. .................. 600/584; 600/583; 606/181; 606/182; 606/184

(58) Field of Classification Search .......... 600/181, 600/583, 584; 606/181, 182, 184
See application file for complete search history.

(56) References Cited

U.S. PATENT DOCUMENTS

| | | | |
|---|---|---|---|
| 4,503,856 A | 3/1985 | Cornell et al. | |
| 4,517,978 A | 5/1985 | Levin et al. | |
| 4,580,564 A * | 4/1986 | Andersen ................. | 606/172 |
| 4,637,403 A | 1/1987 | Garcia et al. | |
| 5,320,607 A | 6/1994 | Ishibashi | |
| 5,356,420 A * | 10/1994 | Czernecki et al. ......... | 606/182 |
| 5,368,047 A | 11/1994 | Suzuki et al. | |
| 5,487,748 A | 1/1996 | Marshall et al. | |
| 5,662,127 A | 9/1997 | DeVaughn | |
| 5,951,493 A | 9/1999 | Douglas et al. | |
| 6,248,120 B1 * | 6/2001 | Wyszogrodzki .......... | 606/182 |
| 6,432,120 B1 | 8/2002 | Teo | |
| 6,540,763 B2 * | 4/2003 | Teo et al. ................. | 606/182 |
| 6,837,858 B2 | 1/2005 | Cunningham et al. | |
| 6,866,641 B2 * | 3/2005 | Marshall .................. | 600/583 |
| 7,160,313 B2 * | 1/2007 | Galloway et al. .......... | 606/167 |
| 7,316,698 B1 * | 1/2008 | Galloway et al. .......... | 606/167 |
| 7,322,997 B2 * | 1/2008 | Shi ........................ | 606/181 |
| 7,452,365 B2 * | 11/2008 | Galloway et al. .......... | 606/167 |
| 7,494,498 B2 * | 2/2009 | Lipoma et al. ............ | 606/182 |
| 7,575,583 B1 * | 8/2009 | Schraga .................. | 606/182 |
| 2004/0039407 A1 * | 2/2004 | Schraga .................. | 606/181 |
| 2004/0186394 A1 * | 9/2004 | Roe et al. ................. | 600/583 |
| 2004/0260204 A1 | 12/2004 | Boecker et al. | |
| 2006/0200181 A1 * | 9/2006 | Fukuzawa et al. ........ | 606/181 |

FOREIGN PATENT DOCUMENTS

| | | |
|---|---|---|
| WO | 9906827 | 2/1999 |
| WO | 03049613 | 6/2003 |
| WO | 03092512 | 11/2003 |

OTHER PUBLICATIONS

PCT Search Report Aug. 16, 2006.

* cited by examiner

*Primary Examiner*—Max Hindenburg
*Assistant Examiner*—Sean P Dougherty
(74) *Attorney, Agent, or Firm*—Dority & Manning, P.A.

(57) ABSTRACT

A blood sampling device includes a lancet having a skin piercing member disposed at an end thereof. The lancet is slidable within and releasably engaged with an elongated lancet guide that remains stationary with use of the device. A shell is axially movable relative to the lancet guide between a rest position and an actuate position, with the lancet being spring loaded within the lancet guide by movement of the shell from the rest position to the actuate position.

11 Claims, 6 Drawing Sheets

DEVICE FOR SAMPLING BLOOD

BACKGROUND OF THE INVENTION

Many health care tests (e.g., cholesterol, glucose, etc.) require a blood sample as the source of the analyte. Typically, the blood is withdrawn via an intravenous cannula or syringe wherein a vacuum tube is used to withdrawn and store the blood. This method, however, is not well suited for all individuals, particularly infants, elderly individuals, or ill individuals who cannot afford or are physically incapable of furnishing the required amount of blood. Also, many blood tests do not require the relatively large amount of blood withdrawn via the intravenous method.

As a result, blood lancets have been developed for withdrawing capillary blood, usually from an individual's fingertip (the "finger prick" method). These devices are more cost effective and generally less traumatic to the individual in obtaining blood samples of up to about 50 microliters. Conventional lancets typically employ a needle or blade at the end of an elongated rigid member that is essentially jabbed into the fingertip by a technician. A vial or blood blotter is then used to collect the blood. However, this procedure also has drawbacks. A successful blood sample depends in large part on the skill of the technician, who must hold the individual's hand and finger steady while accurately "aiming" the lancet and reassuring the patient. The patient's anxiety level can increase rapidly with failed attempts.

Various spring loaded sampling devices have also been developed, particularly for home diagnostic test kits. Reference is made, for example, to U.S. Pat. Nos. 4,503,856; 4,517,978; and 5,487,748. Spring-loaded devices, however, may have a tendency to prematurely actuate, for example when the individual removes the safety cap. Another common failure occurs when, by reflex, the individual pulls back from the lancet just prior to the device being triggered. This results in a grazing nick to the skin, or no skin penetration at all.

With growing demand by consumers, and emphasis by healthcare institutions for individuals to participate in and manage aspects of their own health care, home diagnostic test kits have become increasingly important. The blood sampling devices used with these diagnostic test kits play a significant role in the kit's reliability, accuracy, and acceptance by the consuming public. Thus, a continuous need exists in the art for improved blood sampling devices.

SUMMARY

Objects and advantages of the invention will be set forth below in the following description, or may be obvious from the description, or may be learned through practice of the invention.

The present invention is directed generally to a single-use, disposable blood sampling device. The device is particularly suited for home diagnostic test kits, but is not limited to such use. Additionally, the device is not limited to any particular diagnostic test or protocol. The inventive blood sampling device has usefulness in any procedure where blood must be withdrawn from an individual for any reason.

The present sampling device is also not limited to any particular sampling site on an individual. Fingertip sampling is relatively painful for certain individuals and Alternate Site Testing (AST) is a concept gaining recognition in the medical arts as a preferred method of blood sampling in that it significantly reduces pain and anxiety while reliably producing a sufficient volume of blood for various tests. The sampling device according to the invention is well suited for fingertip sampling as well as AST procedures.

In particular embodiments, a blood sampling device in accordance with the invention includes a lancet having a skin piercing member, such as a blade or needle, disposed at an end thereof. The lancet is disposed within and axially movable relative to an elongated lancet guide. The lancet is releasably engaged with the lancet guide and is released upon actuation of the device, wherein the lancet is propelled through the lancet guide. The lancet guide has a longitudinal end that is placed against the user's skin. This end may include a recessed skin engagement area such that a portion of the user's skin is caused to bulge into the recessed area when the lancet guide is pressed against the skin.

The opposite end of the lancet guide is disposed at least partially within a shell. In operation, the lancet guide is pressed against the user's skin and the shell is movable relative to the lancet guide between a rest position and an actuate position. Movement of the shell between these positions causes a bias element to spring-load the lancet within the lancet guide. Upon the shell being pushed by the user to its actuate position, the lancet is automatically released from the lancet guide and is propelled forward within the lancet guide a sufficient distance such that the skin piercing member pierces the user's skin.

The lancet is engaged within the lancet guide by any suitable releasing mechanism or catch. The catch holds the lancet within the lancet guide until sufficient spring force is built up with movement of the shell from its rest position to the actuate position, at which point the catch releases the lancet. In a particular embodiment, the catch comprises a cantilevered clip engaged within a recess in the lancet. The clip may be formed integrally with the lancet guide, or attached to the guide, and include an angled engagement surface. A release member may be configured integrally with the shell and may be, for example, a wedge surface that engages the angled engagement surface on the clip to move the clip out of the recess in the lancet.

The lancet guide serves to retain and guide the lancet. It should be understood that various structural embodiments may be utilized for this purpose. In a particular embodiment, the lancet guide is an open-ended longitudinally extending member, such as a cylinder member, and the lancet is axially slidable within the open-ended member. The bias element may be a spring that extends through a longitudinal end of the lancet guide with one end of the spring engaged against the lancet and the opposite end of the spring engaged with the shell.

Guide structure, such as tracks or the like, may be provided within the shell along the lancet guide. This guide structure may stabilize movement of the shell relative to the lancet guide.

The shell may take on any form or shape. In particular embodiments, the shell also defines an outer housing member that is grasped by the user. In alternate embodiments, the shell may be contained within another member, such as a separate housing member.

In a particular embodiment, the lancet is loaded within the lancet guide and propelled by a spring operably disposed between the lancet and the shell that is moved axially relative to the lancet guide. The spring is designed with a length and spring constant such that, after actuation, the spring retracts the piercing member back into the lancet guide as the spring returns to its equilibrium state even with the shell being held in its actuate position by the user.

It should be appreciated that the blood sampling device according to the invention may be provided as a stand-alone component, or may be incorporated into any manner of blood testing device. For example, the blood sampling device may be configured as an integral component of any manner of lateral flow assay device. The blood sampling device may be configured at one end of the assay, with the assay housing defining the shell member. In an alternate embodiment, the blood sampling device may be attachable to a blood testing device, for example by a press-fit onto the end of the blood testing device. The shell or housing of the blood sampling device may include a recess or other structure that allows it to attached directly onto the housing of a separate test device, such as a lateral flow assay device. The blood sampling device is not limited to any particular type of blood testing device, and may be incorporated into or attached to any test device that requires a sample of the user's blood.

Various features and aspects of the present invention are discussed in greater detail below.

BRIEF DESCRIPTION OF THE DRAWINGS

A full and enabling disclosure of the present invention, including the best mode thereof, directed to one of ordinary skill in the art, is set forth in the specification, which makes reference to the appended drawings, in which.

Repeat use of reference characters in the present specification and drawings is intended to represent the same or analogous features or elements of the invention.

DETAILED DESCRIPTION

Reference now will be made in detail to embodiments of the invention, one or more examples of which are illustrated in the drawings. Each example is provided by way of explanation of the invention, not limitation of the invention. In fact, it will be apparent to those skilled in the art that various modifications and variations can be made in the present invention without departing from the scope or spirit of the invention. For instance, features illustrated or described as part of one embodiment, can be used with another embodiment to yield a still further embodiment. Thus, it is intended that the present invention covers such modifications and variations as come within the scope of the appended claims and their equivalents.

Figure 1:
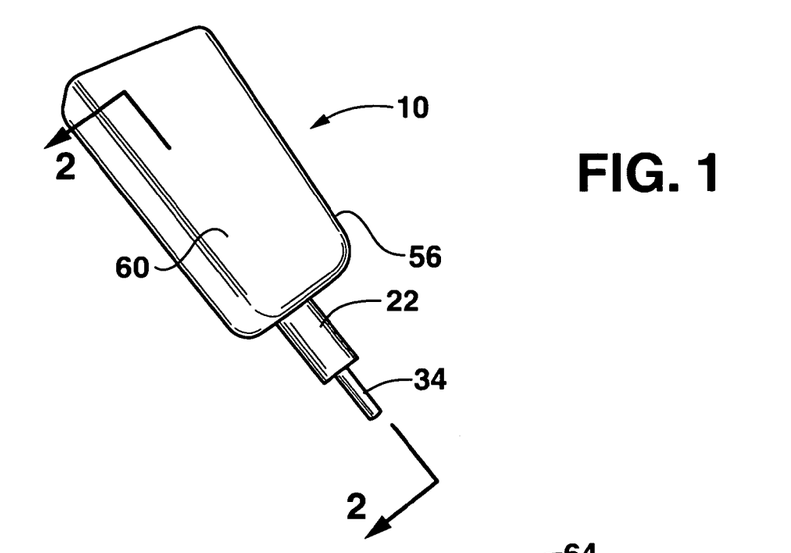
FIG. 1 is a perspective view of a blood sampling device according to the invention.

FIG. 1 illustrates an embodiment of a blood sampling device 10 in accordance with aspects of the invention. The device 10 is a relatively small, portable, and disposable single-use blood sampling device that is particularly suited for home diagnostic test kits, but it is not limited to such use. The device 10 includes a housing 60 of any desired shape and configuration. The housing 60 is preferably designed so as to be easily grasped and handled with a single hand. A lancet guide 22 extends from a forward end of the housing 60, and will be described in greater detail below. A safety cap 34 is provided with the device 10 and is removed prior to use of the device, as described in greater detail below.

Figure 2:
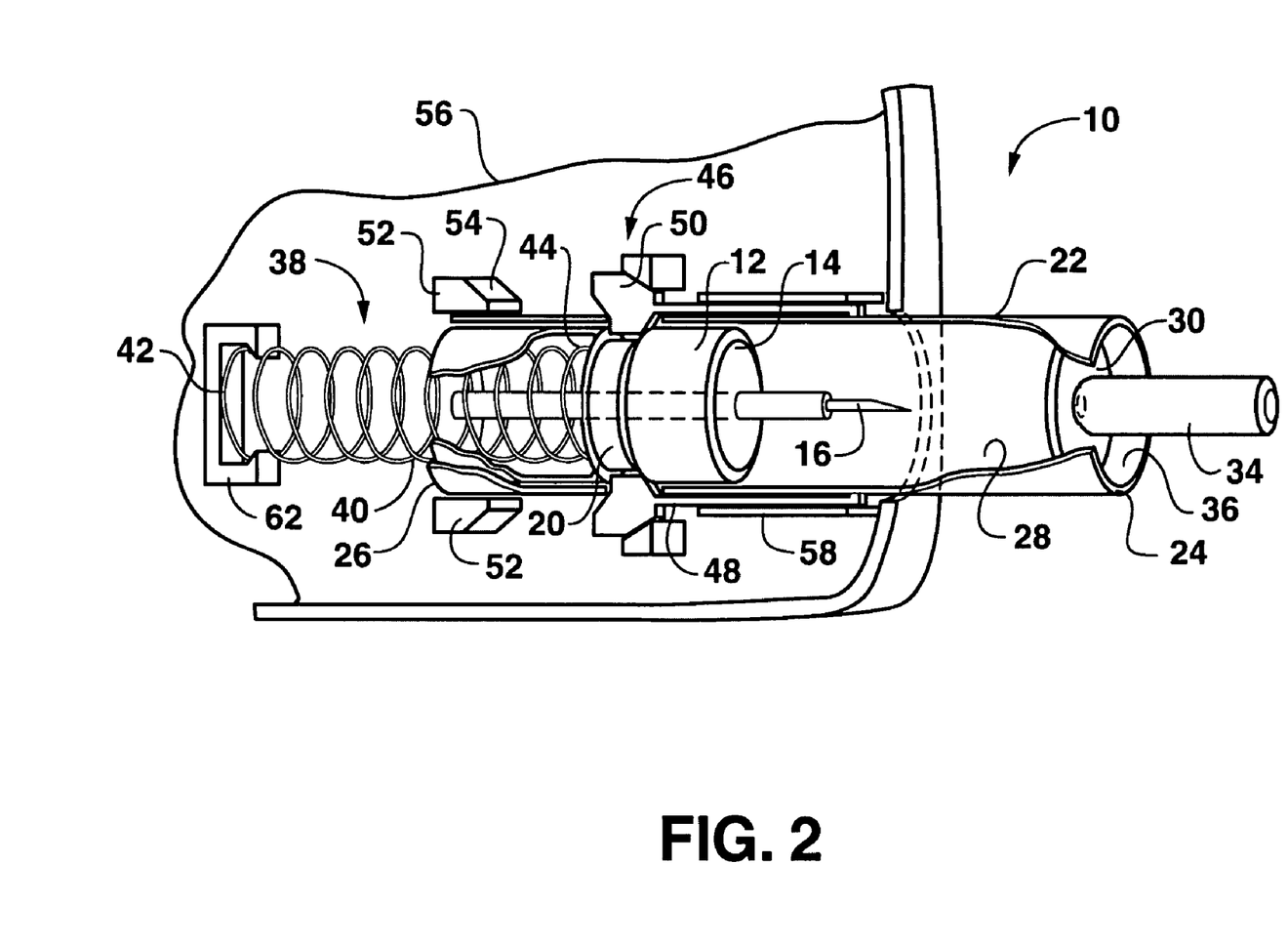
FIG. 2 is a cross-sectional perspective view of the blood sampling device taken along the lines indicated in FIG. 1

FIG. 2 is a cross-section view of an embodiment of the blood sampling device 10. A lancet 12 includes a skin piercing member 16, such as a trocar, needle, blade, or the like, extending from a forward facing hub 14. A circumferential groove or recess 20 is provided at the opposite end of the lancet 20. The purpose of this groove 20 will be explained below.

The lancet 12 is disposed within the elongated lancet guide 22. The lancet 12 is releasably held within the space 28 of the lancet guide 22 until actuated, at which time the lancet 12 is propelled forward within the lancet guide 22 to such an extent that the piercing member 16 pierces the skin of a user. The lancet guide 22 includes a first longitudinal end 24 that is placed against the user's skin, as particularly illustrated in FIG. 3E. At the longitudinal end 24 of the lancet guide 22, a recessed skin engagement area 36 is circumscribed by the longitudinal end structure 24, which is pressed against the user's skin. A hub or plate 30 defines the end of the recessed skin engagement area 36 and includes a hole 32 through which the skin piercing member 16 extends in the actuated position of the device 10. The hole 30 is exposed once the user removes the safety cap 34.

The lancet guide 22 includes an opposite longitudinal end 26 that is disposed within a shell 56. The shell 56 may constitute the same structure as the housing 60 illustrated in FIG. 1. In an alternate embodiment, the shell 56 may be a separate structure contained within the housing 60. The shape or configuration of the shell 56 may vary widely within the scope and spirit of the invention. In general, the shell 56 serves to spring-load the lancet 12 within the lancet guide 22, and to actuate the device 10, as described in greater detail below.

Figure 3A:
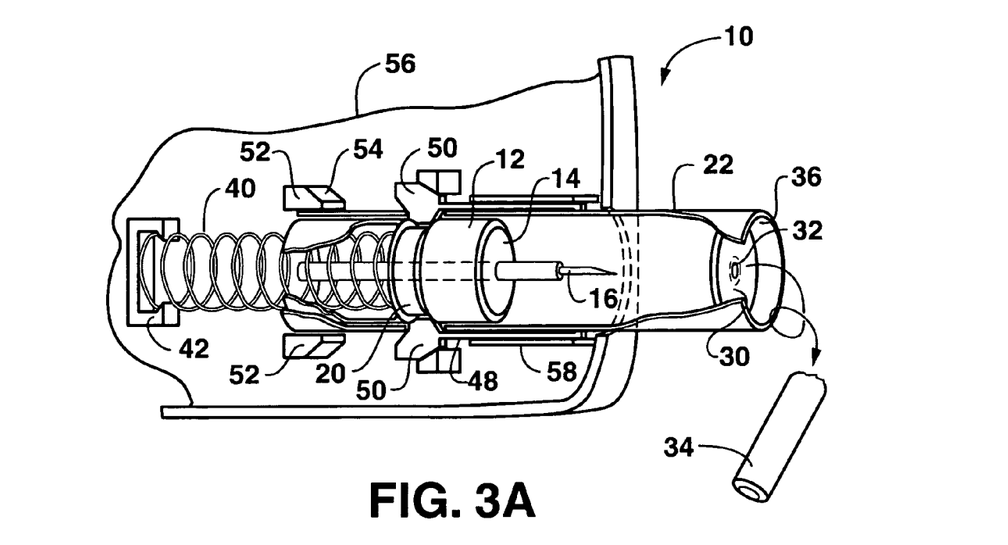
FIGS. 3A through 3G are sequential operational views of the blood sampling device.
Figure 3B:
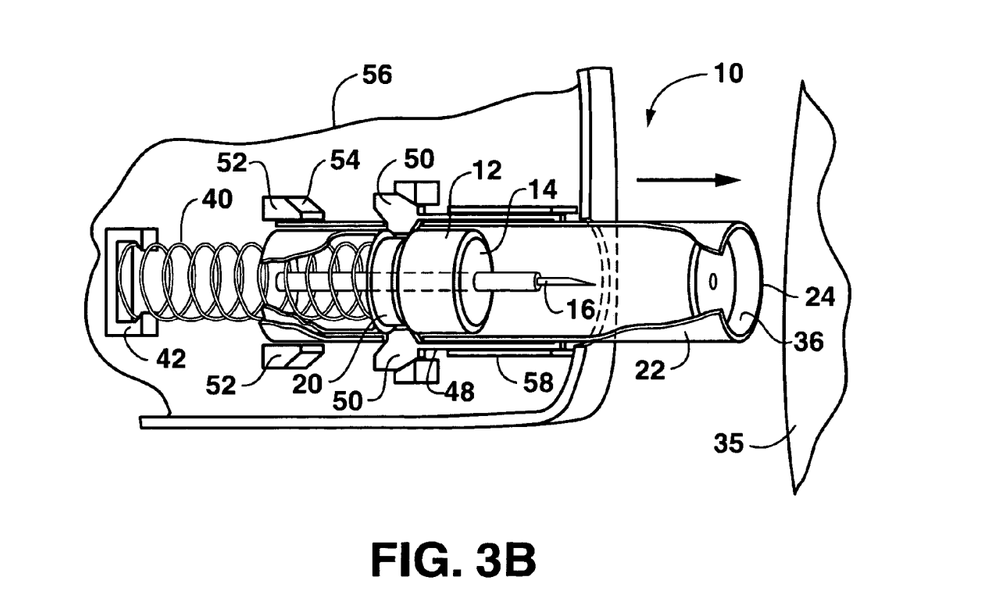
Figure 3C:
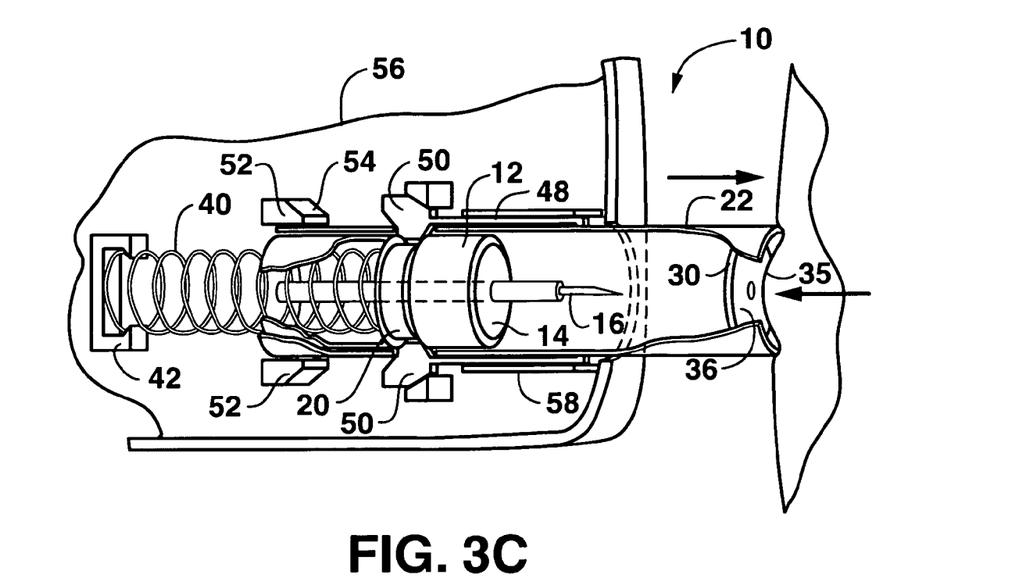
Figure 3D:
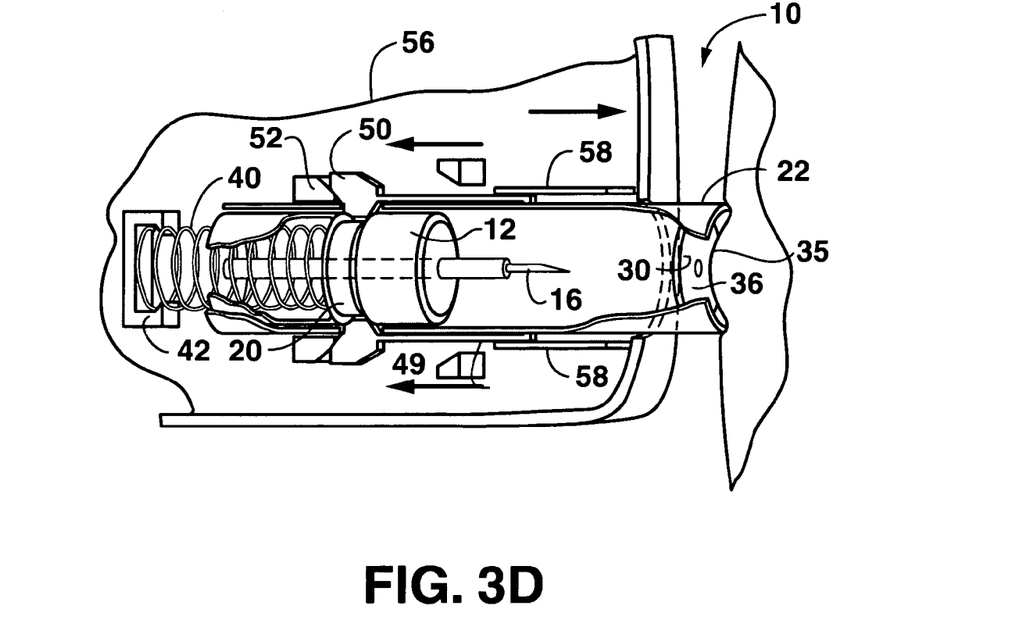
Figure 3E:
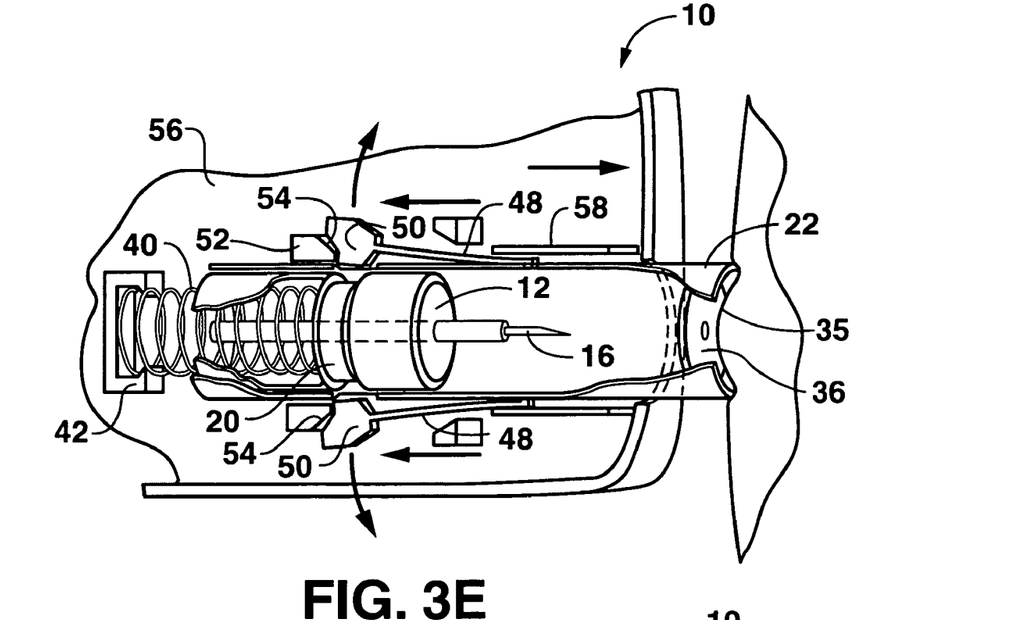

In operation, the shell 56 is movable or slidable along the lancet guide 22 between a rest position (FIG. 3B) and an actuate position (FIG. 3E). Movement of the shell 56 between these positions causes a bias element 38 to spring-load the lancet 12 within the lancet guide 22. In the illustrated embodiments, the bias element 38 is a spring 40, but may be a spring washer, resilient material, or any other suitable biasing element. The spring 40 includes a first end 42 that is retained or secured to the shell 56 by any conventional means, including a retaining clip 62 as illustrated in the figures. The opposite end 44 of the spring 40 is disposed against the back end of the lancet 12, and may be attached to a hub or other structure on the lancet 12.

The lancet 12 is releasably engaged within the lancet guide 22 by any suitable releasing mechanism or catch 46. The catch 46 holds the lancet 12 within the lancet guide 22 until sufficient spring force is built up with movement of the shell 56 from its rest position to its actuate position. At the actuate position, the catch 46 automatically releases the lancet 12, which is propelled forward within the lancet guide 22. In the illustrated embodiment, the catch 46 is defined by cantilevered arms or clips 48 that are engaged within the recess 20 in the lancet 12. The cantilevered clips 48 include an engagement head 50 at the end thereof. The cantilevered clips 48 are configured with the lancet guide 22, and may be defined by slits in the side wall of the lancet guide 22. In an alternate embodiment, the cantilevered clips 48 may be separate members that are attached to the lancet guide 22. A complimentary release member 52 is configured with the shell 56 to engage the catch 46 at the actuate position of the shell 56. In the illustrated embodiment, the release member 52 is defined by a relatively simple block that may include an angled wedge surface 54. As the shell 56 is advanced forward relative to the lancet guide 22, the release member 52 will contact the engagement head 50 of the cantilevered clips 48. Further advancement of the shell 56 causes the wedge surfaces 54 to force the cantilevered clips 48 radially outward to such an extent that the engagement heads 50 move out of the recess 20 in the lancet guide 12.

The shell 56 may also include any manner of guide structure 58 along any portion of the length of the lancet guide 22. This guide structure 58 may include track members or the like to help ensure relatively smooth sliding movement between the shell 56 and the lancet guide 22.

FIGS. 3A through 3G are sequential operational views of the embodiment of the blood sampling device 10 illustrated in the figures. Referring to FIG. 3A, the shell 56 is illustrated in its rest position relative to the lancet guide 22. The safety cap 34 is illustrated as being removed from the hub 30 so as to expose the hole 32. Safety cap 34 may be a member that is integrally molded with the lancet guide 22 or the hub 30 and is easily broken off prior to use of the device 10. In an alternate embodiment, the safety cap 34 may be a tubular member that extends through the lancet guide 22 and is attached to lancet 12 or to the piercing member 16. In this embodiment, any manner of structure, such as block member 49 in FIG. 3D, may be used to prevent movement of the lancet guide 22 and lancet 12 when removing the safety cap 34. It should be appreciated that any number of devices may function as a safety cap 34, including a removable seal, plug, and so forth.

FIG. 3B illustrates the device 10 in its initial position adjacent to the skin 35 of a user, for example by the user simply grasping the shell 56 (which may also constitute the housing 60 illustrated in FIG. 1) and moving the device towards their finger or an alternate test site.

FIG. 3C illustrates the device 10 as the lancet guide 22 is initially placed against the skin 35 of the user. The recessed skin engagement area 36 is circumscribed by the end 24 of the lancet guide 22, and the user's skin 35 is thus forced to bulge inward into the recessed skin engagement area 36 towards the plate 30. At this point, the lancet guide 22 remains stationary relative to the patient's skin 35 during further actuation of the device 10.

FIG. 3D illustrates the shell 56 being advanced from its rest position of FIG. 3C towards its actuate position. As the shell 56 is advanced, it slides relative to the lancet guide 22 while the lancet 12 is retained in its axial position relative to the lancet guide 22 by engagement of the head 50 of the cantilevered clips 48 within the recess 20 defined in the lancet 12. Still referring to FIG. 3D, axial movement of the shell 56 towards its actuate position results in the spring 40 being compressed between the retaining clip 42 and the back surface of the lancet 12, thereby spring-loading the lancet 12 within the lancet guide 22.

FIG. 3E illustrates the shell 56 at its actuate position relative to the lancet guide 22. At this position, the release members 52 that are configured on the shell 56 are moved into contact against the engagement heads 50. The wedge surfaces 54 of the release member 52 contact against complimentary surfaces of the engagement heads 50 and thus cause the heads and cantilevered arms 48 to spread radially outward until the heads 50 are moved radially out of the groove 20 in the lancet 12. At this point, the lancet 12 is released and propelled forward within the lancet guide 22, as particularly illustrated in FIG. 3F.

Figure 3F:
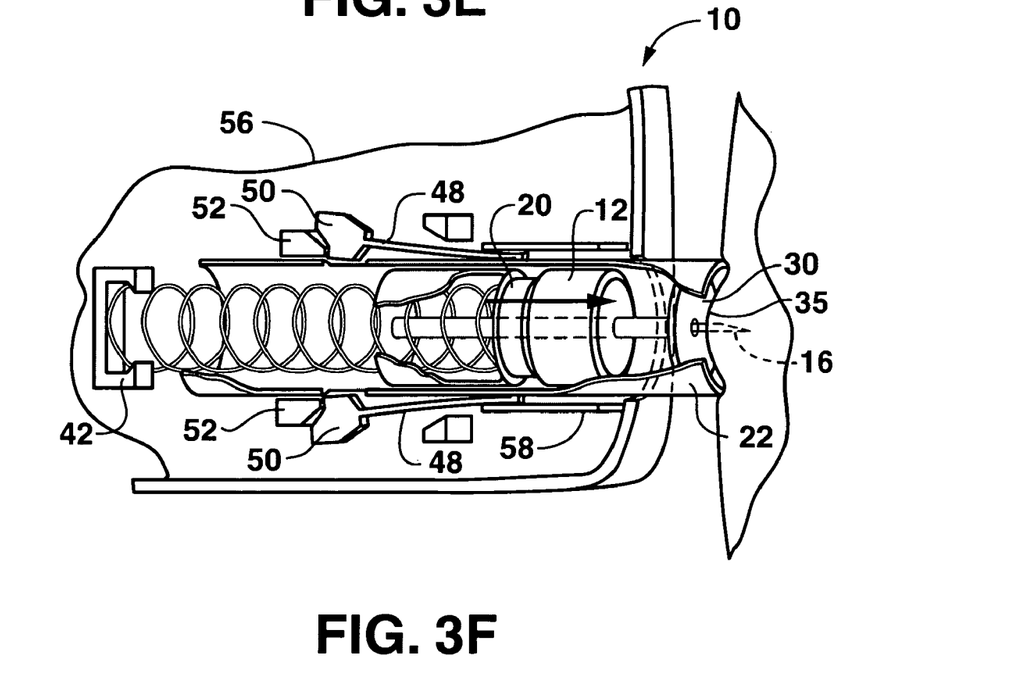

Referring to FIG. 3F, the lancet guide 20 is propelled forward by the spring 40 to such an extent that the skin piercing member 16 extends through the hole 32 in the plate 30 and pierces the user's skin 35 within the recessed skin engagement area 36. The spring 40 is designed so as to have a length and spring constant such that the spring is in an overextended condition at the actuate position of the shell 56 illustrated in FIG. 3F. The spring will thus retract to an equilibrium position and withdraw the lancet 20 back into the lancet guide 22 a sufficient distance so that the skin piercing member 16 is withdrawn from the user's skin 35 even if the shell 56 is maintained by the user in its actuate position. In other words, the piercing member 16 does not remain penetrated into the user's skin 35 after the lancet 12 is triggered, but is automatically withdrawn from the user's skin with no further action by the user.

Figure 3G:
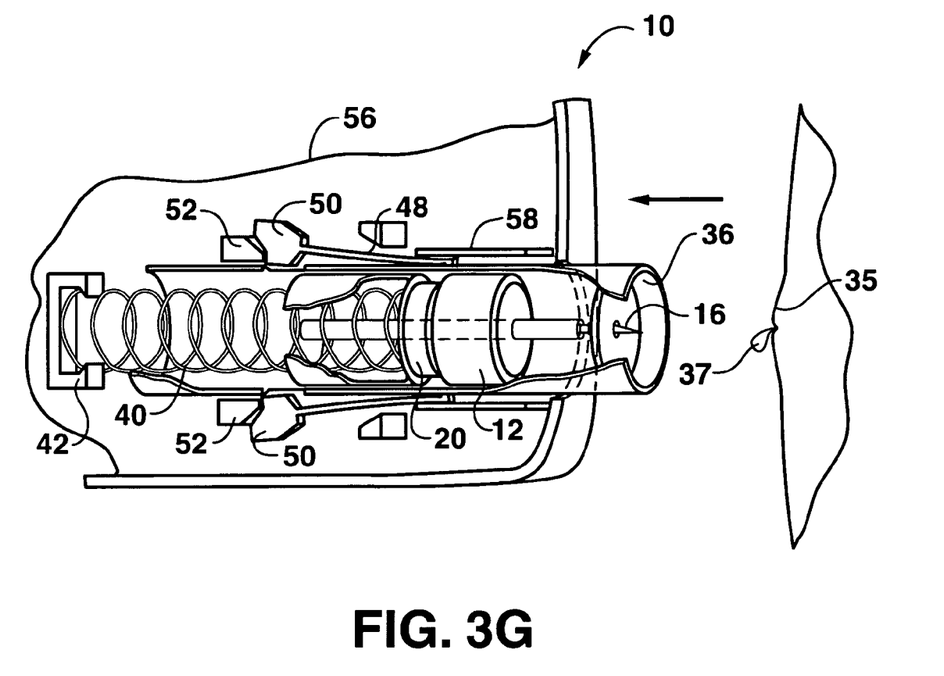

FIG. 3G illustrates the device 10 after it has been actuated and particularly illustrates the position of the piercing member 16 withdrawn back into the lancet guide 22 through the hole 32. At this point, the user simply moves the shell 56 away from the skin 35 and blood 37 is free to flow from the penetration site.

Figures 4A, 4B:
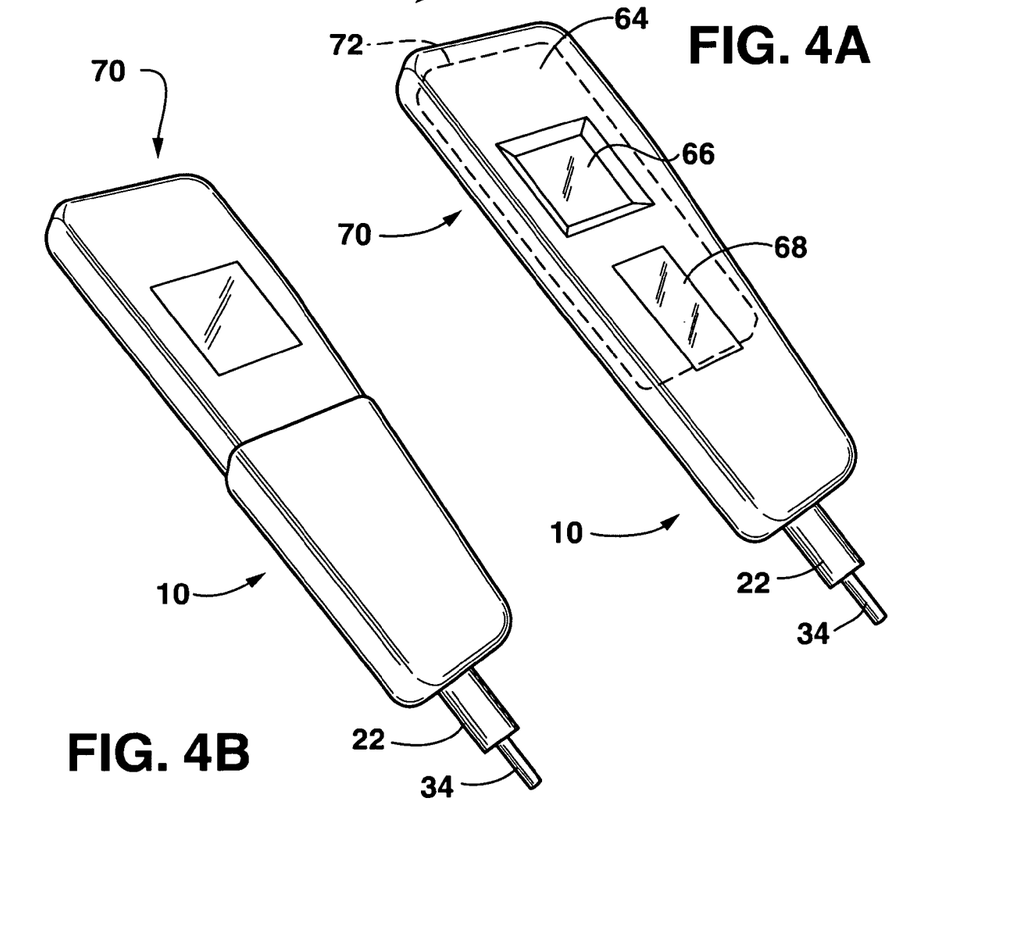
FIG. 4A is a perspective view of a lateral flow assay device incorporating a blood sampling device in accordance with the invention.
FIG. 4B is a perspective view of a blood sampling device attachable to a separate lateral flow assay device.

The blood sampling device 10 according to the invention may be provided to consumers as a stand alone device, such as the device illustrated in FIG. 1. However, it should also be appreciated that the sampling device 10 may be incorporated into an actual blood testing device. For example, the blood sampling device 10 may be configured as an integral component of any manner of construction of conventional blood testing devices. Referring to FIG. 4A for example, a lateral flow assay device 70 is illustrated that incorporates the blood sampling device 10 according to the invention as an integral component. Lateral flow assay devices are known by those skilled in the art and various embodiments of such devices are commercially available. In general, the lateral flow assay 70 includes a housing in which is disposed an assay strip 72. In certain embodiments, the assay strip 72 is configured for detection of specific antibodies in human serum or whole blood samples. The assay strip 72 works on the principle of binding the specific antibodies to a broadly reactive antigen carried by the assay strip 72. In the embodiment illustrated in FIG. 4A, the housing of the assay 70 includes an elongated portion 64 of the same housing that constitutes the shell 56 for the blood sampling device 10. A sample well 66 is provided in the extended housing portion 64 into which a blood sample is deposited by, for example, a capillary tube. A window 68 is provided in the housing 64 so that the user may view a visible indication of the test results on the assay strip 72.

In the embodiment depicted in FIG. 4B, the blood sampling device 10 is a separate component from the lateral flow assay 70, but is configured to be easily attached to the assay 70. For example, the housing of the sampling device 10 may include a recess in an end of the housing that is sized to allow the sampling device to be press fitted onto an end of the assay 70, as depicted in FIG. 4B. In an alternate embodiment, the recess may be incorporated in the assay 70 and the housing 60 of the sampling device 10 has a size so as to be pressed into the recess. It should be appreciated that any suitable engaging structure may be utilized for this purpose. Alternatively, an adhesive, hook-and-loop, or other attaching device may be used.

It should be appreciated that the particular type of lateral flow assay 70 or other blood sampling device, or principle of operation, is not particularly relevant to the scope of the invention. The invention includes any blood testing device that incorporates the unique sampling device according to the invention as an integral component or separate but attachable component.

It should be appreciated by those skilled in the art that various modifications and variations can be made to the embodiments of the invention illustrated or described herein without departing from the scope and spirit of the invention.

What is claimed is:

1. A blood sampling device, comprising:

a lancet having a first end and a second end opposite the first end, and a skin piercing member disposed at said first end;

an elongated lancet guide, said lancet disposed with said first and second ends within said lancet guide and axially movable relative to said lancet guide;

a shell, said lancet guide disposed at least partially within said shell with a first longitudinal end of said lancet guide extending from said shell and placed against a user's skin in operation of said sampling device, said shell axially movable relative to said lancet guide from a rest position to an actuate position;

a bias element disposed between said second end of said lancet and a stop on said shell;

a releasable catch configured on said lancet guide, said catch extending radially into said lancet guide and engaged with said lancet between said first and second ends of said lancet in a rest position of said lancet such that said lancet does not move relative to said lancet guide in said rest position, and a release member configured on said shell so as to directly contact and release said catch in said actuate position of shell;

wherein in use of said blood sampling device, forced movement of said shell relative to said lancet guide loads said bias element against said lancet until said release member directly contacts and releases said catch at said actuate position of said shell such that said lancet is propelled by said bias element through said lancet guide;

wherein said lancet guide is an open-ended longitudinally extending member, said bias element extending through a second longitudinal end of said lancet guide and disposed against said lancet;

wherein said lancet guide comprises a recessed skin engagement area defined between said first longitudinal end of said lancet guide and a plate member that is spaced axially from said first longitudinal end of said lancet guide, said plate member comprising an opening through which said skin piercing member extends into said skin engagement area in the actuate position of said lancet guide; and wherein said shell defines an outer housing, said blood sampling device further comprising a blood testing device configured with said housing.

2. The blood sampling device as in claim 1, wherein said shell comprises guide tracks along said lancet guide.

3. The blood sampling device as in claim 1, wherein said catch comprises a cantilevered clip engaged within a recess in said lancet.

4. The blood sampling device as in claim 3, wherein said clip comprises an angled engagement surface, and said release member comprises a wedge surface that engages said angled engagement surface on said clip to move said clip out of said recess in said lancet.

5. The blood sampling device as in claim 1, further comprising a safety cap attached to said first longitudinal end of said lancet guide.

6. The blood sampling device as in claim 1, wherein said bias element comprises a spring having an end attached to said lancet.

7. The blood sampling device as in claim 6, wherein said spring comprises a length and spring constant such that said piercing member is withdrawn back into said lancet guide after actuation with said shell at said actuate position.

8. The blood sampling device as in claim 1, wherein the blood testing device is contained within an elongated portion of said outer housing.

9. The blood sampling device as in claim 1, wherein said blood testing device comprises a lateral flow assay strip.

10. The blood sampling device as in claim 1, wherein said blood testing device is separate from and attachable to said outer housing.

11. The blood sampling device as in claim 1, wherein said bias element comprises a single spring configured to overextend in the actuate position and retract to an equilibrium position within the lancet guide a sufficient distance so that the skin piercing member is withdrawn from said opening in said plate member.

* * * * *